United States Patent
Mohammed (10) Patent No.: US 12,196,646 B1
(45) Date of Patent: Jan. 14, 2025

(54) MICROORGANISM SAMPLING TOOL

(71) Applicant: KING SAUD UNIVERSITY, Riyadh (SA)

(72) Inventor: Norah Ali Mohammed, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 18/793,613

(22) Filed: Aug. 2, 2024

(51) Int. Cl.
*G01N 1/04* (2006.01)
*C12Q 1/24* (2006.01)

(52) U.S. Cl.
CPC .................. *G01N 1/04* (2013.01); *C12Q 1/24* (2013.01)

(58) Field of Classification Search
None
See application file for complete search history.

(56) References Cited

U.S. PATENT DOCUMENTS

| | | | | |
|---|---|---|---|---|
| 4,735,905 | A * | 4/1988 | Parker | G01N 1/04 422/534 |
| 7,141,033 | B2 * | 11/2006 | Kanjilal | A61B 10/0038 73/863.52 |
| 7,794,410 | B2 * | 9/2010 | Mikulka | A61B 10/0283 600/564 |

FOREIGN PATENT DOCUMENTS

| | | |
|---|---|---|
| CN | 201230885 Y | 5/2009 |
| CN | 208776702 U | 4/2019 |
| CN | 209470927 U | 10/2019 |
| CN | 210414803 U | 4/2020 |
| CN | 210802949 U | 6/2020 |
| CN | 213309918 U | 6/2021 |
| CN | 215349084 U | 6/2021 |
| CN | 113174319 A | 7/2021 |
| CN | 214361342 U | 10/2021 |
| CN | 113956961 U | 1/2022 |
| CN | 216621845 U | 5/2022 |
| CN | 217479454 U | 5/2022 |
| CN | 218792331 U | 4/2023 |
| CN | 219250242 U | 6/2023 |
| CN | 219645773 U | 9/2023 |

\* cited by examiner

*Primary Examiner* — Elizabeth A Robinson
*Assistant Examiner* — Brittany I Fisher
(74) *Attorney, Agent, or Firm* — Nath, Goldberg & Meyer; Joshua B. Goldberg (57) ABSTRACT

A sampling tool includes an outer body having first and second sections, the first section having first and second ends, the first end configured to retrieve and retain a sample therein. The second section has first and second end portions, and a third portion located between the first end portion and the second end portion. The second end of the first section is integrally connected to the first end portion of the second section. The second section includes an inner body configured to slidably move out of the first end of the first section and retract into the second section to eject the retrieved and retained at least one sample and to prepare the sampling tool for a subsequent at least one sample to be received therein. In use, the sampling tool extracts a sample of medium and ejects the extracted sample over a determined area.

20 Claims, 8 Drawing Sheets

MICROORGANISM SAMPLING TOOL

FIELD AND BACKGROUND

The disclosure of the present application relates to a sampling tool, and particularly to a sampling tool and a method of using the sampling tool for extracting at least one sample from a medium.

DESCRIPTION OF RELATED ART

Agar is a jelly-like substance derived from seaweed that is used as a solid medium to grow microorganisms like bacteria, fungi, and other tiny organisms. It is used in petri dishes and test tubes because it provides a stable surface for these organisms to grow and multiply. Agar is particularly useful because it remains solid at typical laboratory temperatures but can be melted and poured into petri dishes or test tubes where it solidifies again as it cools. This allows scientists to cultivate and study microorganisms under controlled conditions, helping them understand their behavior and characteristics.

Typically, in a medical lab setting, an agar block (agar medium) with a microorganism sample is removed from a petri dish and transferred onto another petri dish for further study or cultivation. The transfer of the agar block is usually done by a sampling tool such as a puncher. However, punchers commonly used in the field are known to damage the agar blocks due to the rigid material (i.e., stainless steel or other metals) of the punchers; and prevent the agar blocks from being released easily from the punchers.

In light of the above, a need remains for a simple, cost-effective sampling tool and method of using the sampling tool for extracting at least one sample (i.e., microorganism) from a medium (i.e., agar medium).

SUMMARY

The present subject matter relates to a sampling tool which, in one embodiment, includes an outer body. The outer body can include a first section and a second section. The first section can include a first end and a second end. The first end can be configured to retrieve and retain at least one sample therein. The second section can include a first end portion, a second end portion, and a third portion, wherein the third portion can be located between the first end portion and the second end portion. The third portion can include a first periphery region and a second periphery region. A surface of the second periphery region can be perpendicular with a surface of the second end portion. The second end of the first section can be integrally connected to the first end portion of the second section. The second section can include a first elongated slot extending from the second end portion to the first periphery region of the third portion. The second section can also include an inner body. The inner body can include a first distal part region, a second distal part region, and a third part region. The third part region can be between the first distal part region and the second distal part region. The first distal part region can include a solid piece configured to slidably move out of the first end of the first section and retract into the second section to eject the retrieved and retained at least one sample and to prepare the sampling tool for a subsequent at least one sample to be received therein, respectively. The second distal part region can include a pressable knob configured to slidably move toward and away from, to contact and disengage, respectively, the second end portion of the second section. The pressable knob can be further configured to contact a portion of the first elongated slot.

In an embodiment, the first elongated slot can extend from an outer circumferential surface to an inner circumferential surface of the second section.

In another embodiment, the pressable knob can contact the portion of the first elongated slot directly.

In an additional embodiment, the sampling tool can further include a first elongated raised profile extending from the second periphery region to the first periphery region of the third portion.

In a supplementary embodiment, a lower region of the first elongated raised profile can include a second elongated slot extending from the second periphery region to about the first periphery region of the third portion.

In a further embodiment, the at least one sample can be a microorganism sample.

In an embodiment, the third part region of the inner body can include a second elongated raised profile configured to slidably mate with the first elongated slot of the second section.

In another embodiment, the second elongated raised profile can be further configured to slidably mate with the second elongated slot of the first elongated raised profile.

In an additional embodiment, the second elongated raised profile can include a first end region and a second end region. The first end region can be configured to slidably stop at about the first periphery region of the third portion. The second end region can be integrally connected to a bottom surface of the pressable knob.

In a supplementary embodiment, an upper surface of the first elongated raised profile can have at least one recess; and wherein the second elongated raised profile can have at least one depressible button configured to engage with the at least one recess.

In an embodiment, the first end and the second end of the first section can be made of plastic material. The plastic material can be selected from the group consisting of polyethylene, polypropylene, and combinations thereof.

In a further embodiment, the present subject matter relates to a method of using the sampling tool above for extracting at least one sample from a medium, the method includes obtaining a medium. Placing the first end of the first section of the sampling tool above an area of interest on the medium. Pressing the first end of the first section into the area of interest on the medium to obtain at least one extracted sample of the medium inside of the first section. Determining an area to eject the at least one extracted sample of the medium. Placing the first end of the first section above the determined area. Slidably move the solid piece of the first distal part region of the inner body towards and out of the first end of the first section to thereby eject the at least one extracted sample of the medium from the first section.

In an embodiment, prior to the pressing step, simultaneously depressing and moving the at least one depressible button away from the at least one recess toward a direction of the second periphery region of the third portion of the second section to retract the solid piece of the first distal part region into the second section.

In another embodiment, the ejection step can include simultaneously depressing and moving the at least one depressible button away from the at least one recess toward a direction of the first periphery region of the third portion of the second section to slidably move the solid piece of the first distal part region of the inner body towards and out of the first end of the first section to thereby eject the at least one extracted sample of the medium from the first section.

In an additional embodiment, the at least one sample can be a microorganism sample and the medium can be an agar medium.

These and other features of the present subject matter will become readily apparent upon further review of the following specification.

BRIEF DESCRIPTION OF DRAWINGS

Similar reference characters denote corresponding features consistently throughout the attached drawings.

DETAILED DESCRIPTION

The following definitions are provided for the purpose of understanding the present subject matter and for construing the appended patent claims. The definitions are not meant to be limiting to the subject matter described herein.

Definitions

Throughout the application, where systems are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a system or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

FIGS. 1-8 depict, in an embodiment, a sampling tool (100) which includes an outer body. The outer body can include a first section (105) and a second section (110). The first section (105) can include a first end (115) and a second end (120). The first end (115) can be configured to retrieve and retain at least one sample therein (not shown). In an embodiment, the at least one sample can be a microorganism sample which can be grown on a medium such as an agar medium (not shown). The microorganism sample can be selected from the group consisting of bacteria, archaea, fungi, algae, protozoa, viruses, other microorganisms, and combination thereof.

Figure 4:
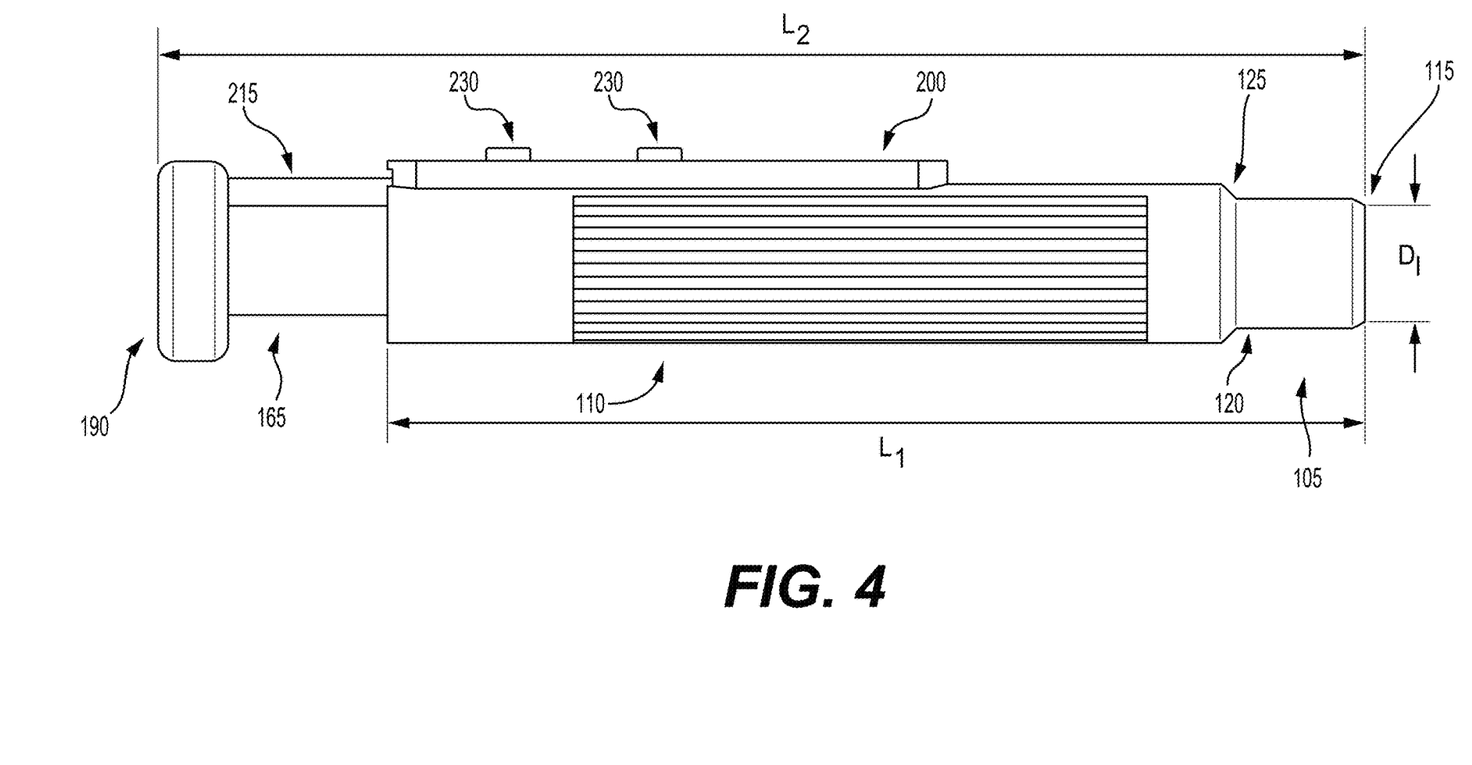
FIG. 4 depicts another view of the sampling tool with dimensions.
Figure 5:
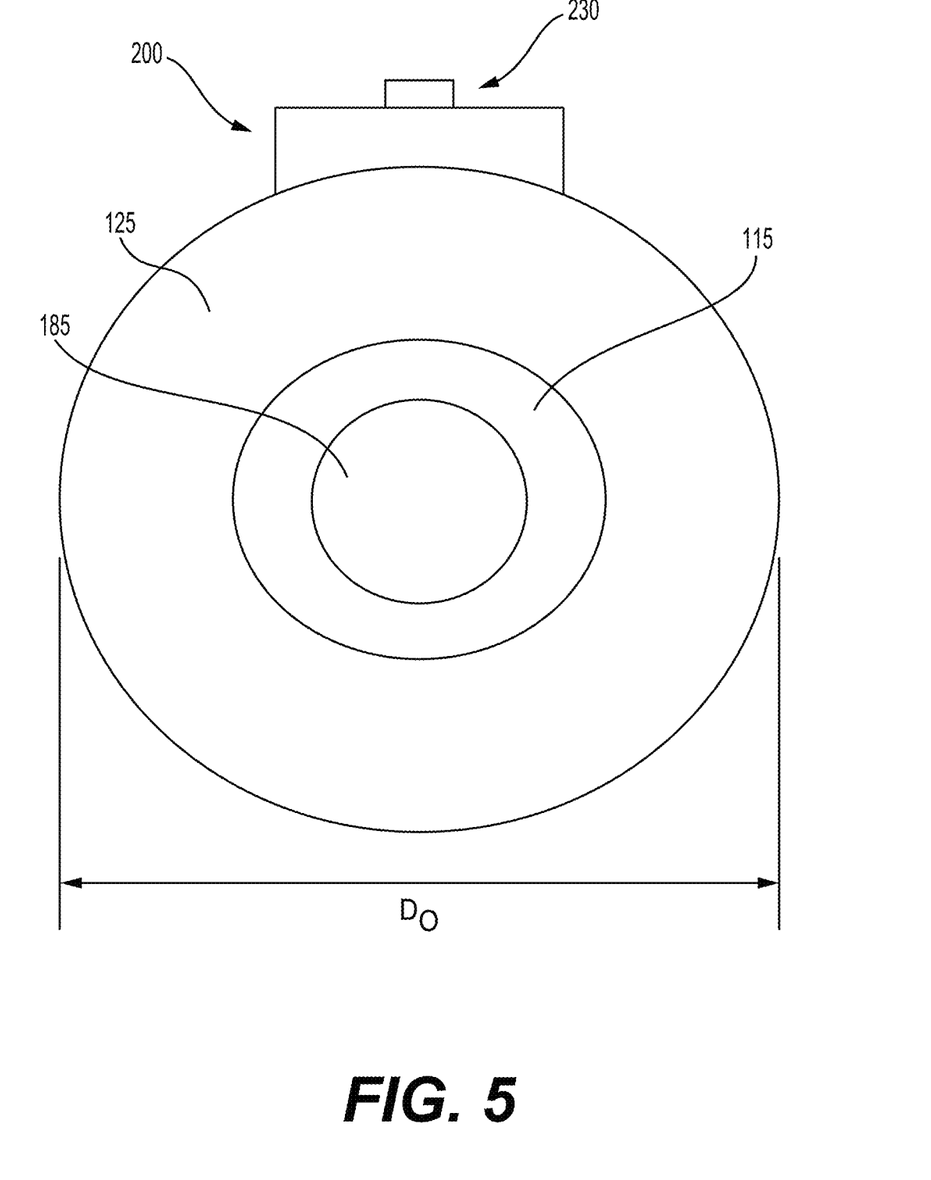
FIG. 5 depicts a front view of the sampling tool.

In a non-limiting embodiment, as shown in FIGS. 4-5, the first end (115) can have an inner diameter (Di) and the second section (110) can have an outer diameter (Do) of about 0.8 cm and about 1.5 cm, respectively. In an embodiment, the sampling tool (100) can be made of plastic, metal, composite, and combination thereof. As a non-limiting example, the sampling tool (100), including the first end (115) and the second end (120) of the first section (105), can be made of plastic. The plastic material can be selected from the group consisting of polyethylene, polypropylene, and combinations thereof.

Figure 1:
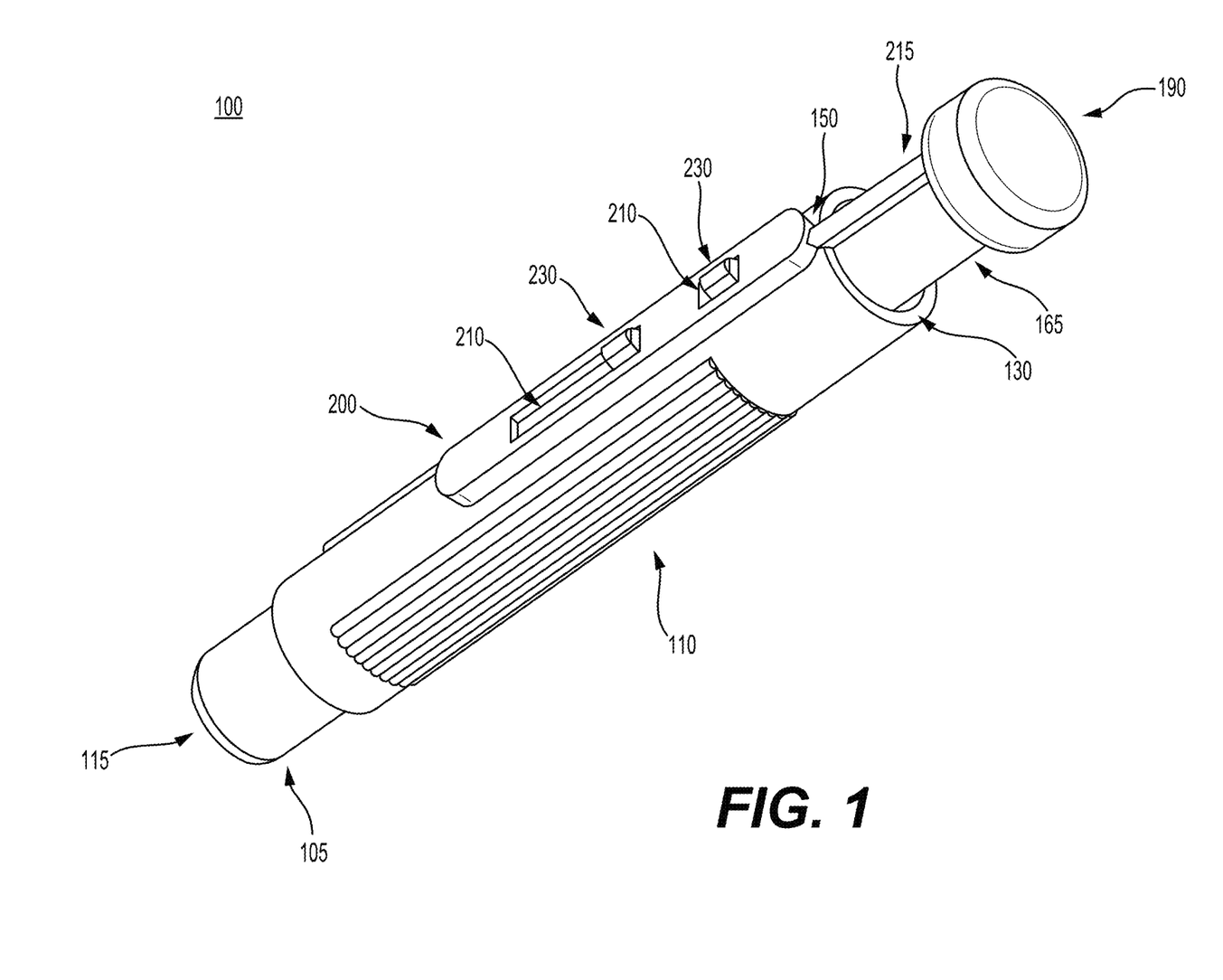
FIG. 1 depicts a side view of the sampling tool of the present subject matter.
Figure 2:
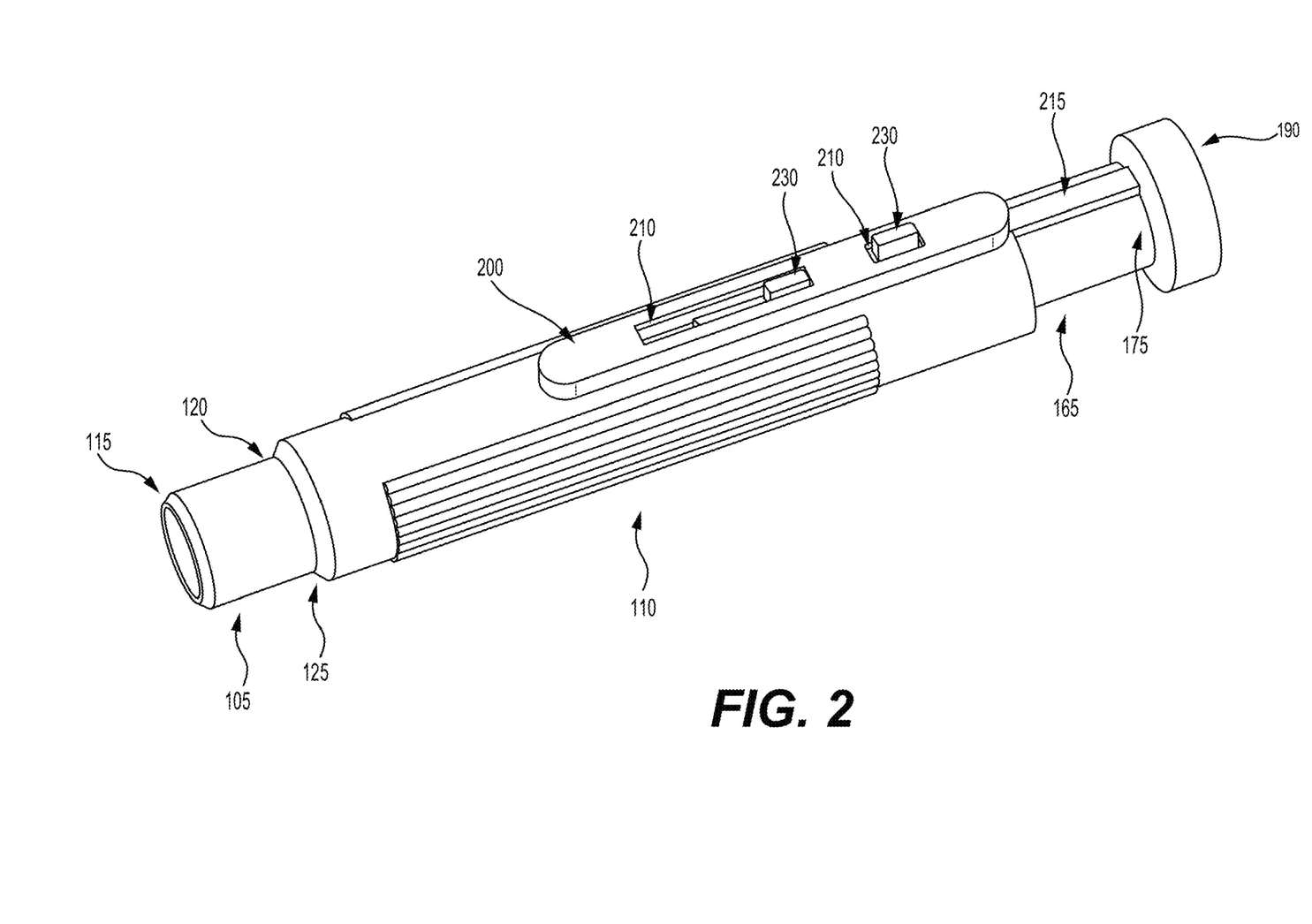
FIG. 2 depicts another side view of the sampling tool with the solid piece of the inner body being retracted at least within the second section of the sampling tool.
Figure 3:
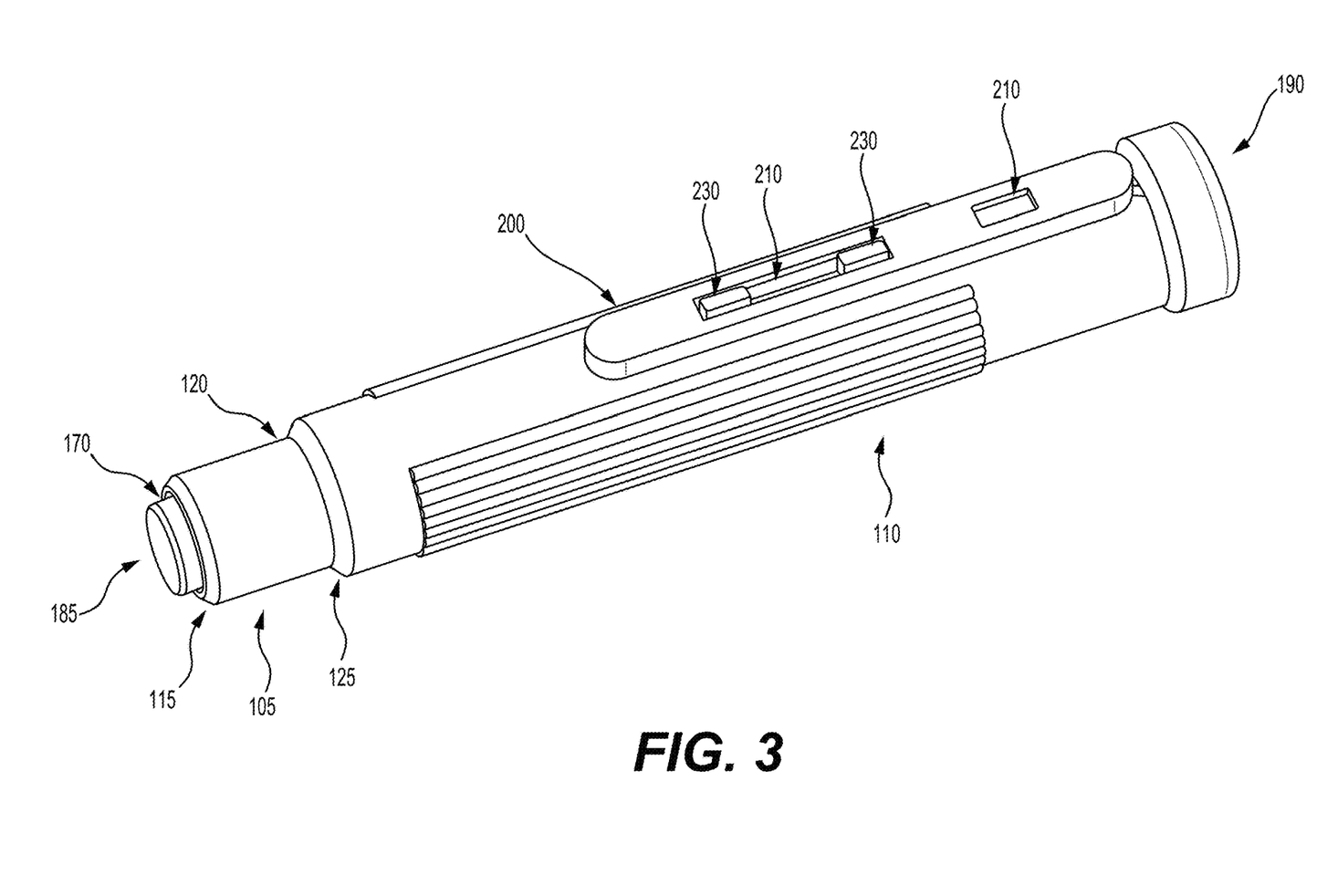
FIG. 3 depicts another side view of the sampling tool with the solid piece of the inner body being outside of the first end of the first section of the sampling tool.
Figure 7:
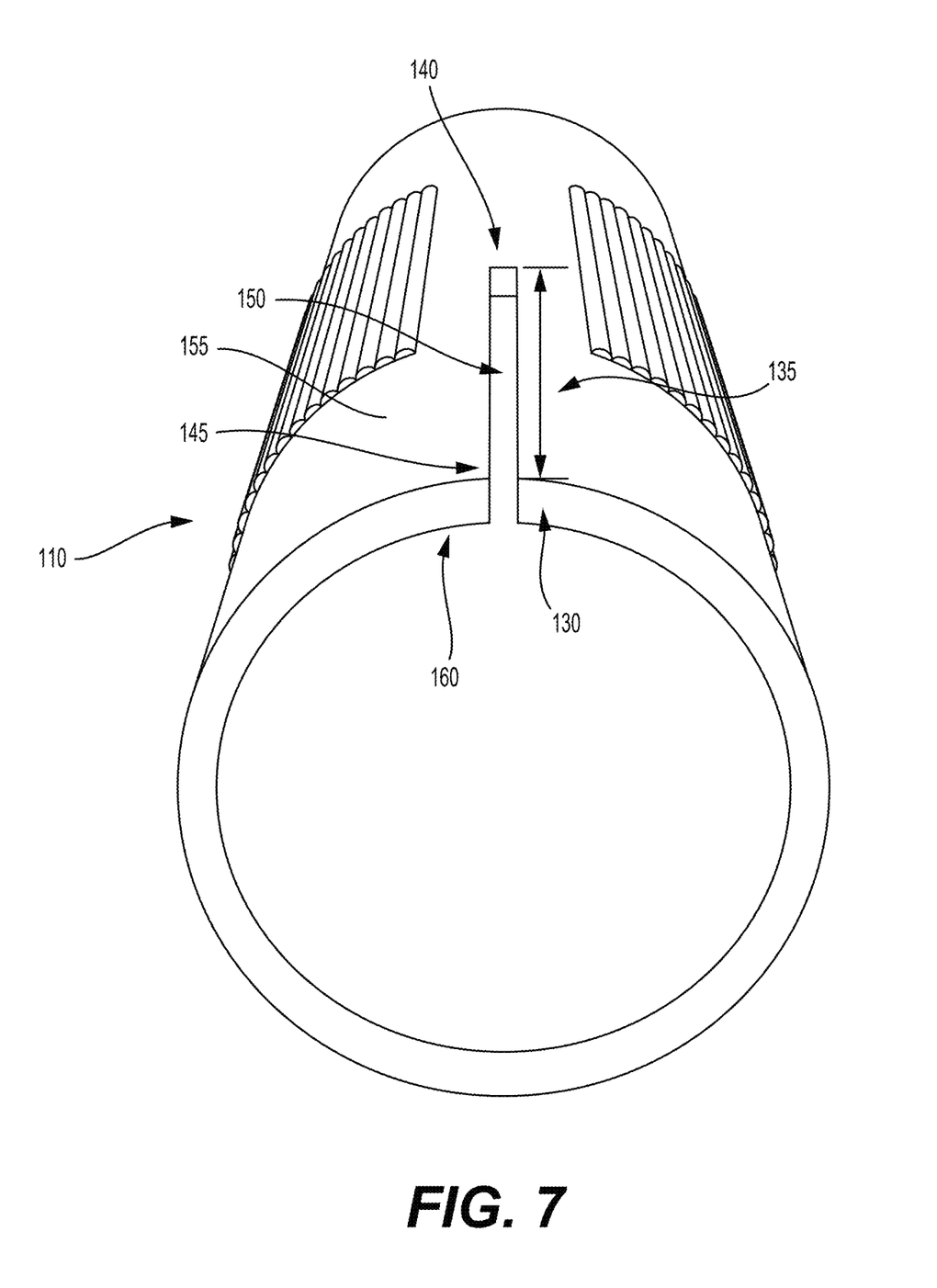
FIG. 7 depicts details of the first elongated slot on the second section.

The second section (110) can include a first end portion (125), a second end portion (130), and a third portion (135), wherein the third portion (135) can be located between the first end portion (125) and the second end portion (130) as shown in FIGS. 1-4 and 7. The third portion (135) can include a first periphery region (140) and a second periphery region (145) as shown in FIG. 7. A surface of the second periphery region (145) can be perpendicular with a surface of the second end portion (130). In FIGS. 2-4, the second end (120) of the first section (105) can be integrally connected to the first end portion (125) of the second section (110).

As shown in FIG. 7, the second section (110) can include a first elongated slot (150) extending from the second end portion (130) to the first periphery region (140) of the third portion (135). The first elongated slot (150) can also extend from an outer circumferential surface (155) to an inner circumferential surface (160) of the second section (110).

Figure 6:
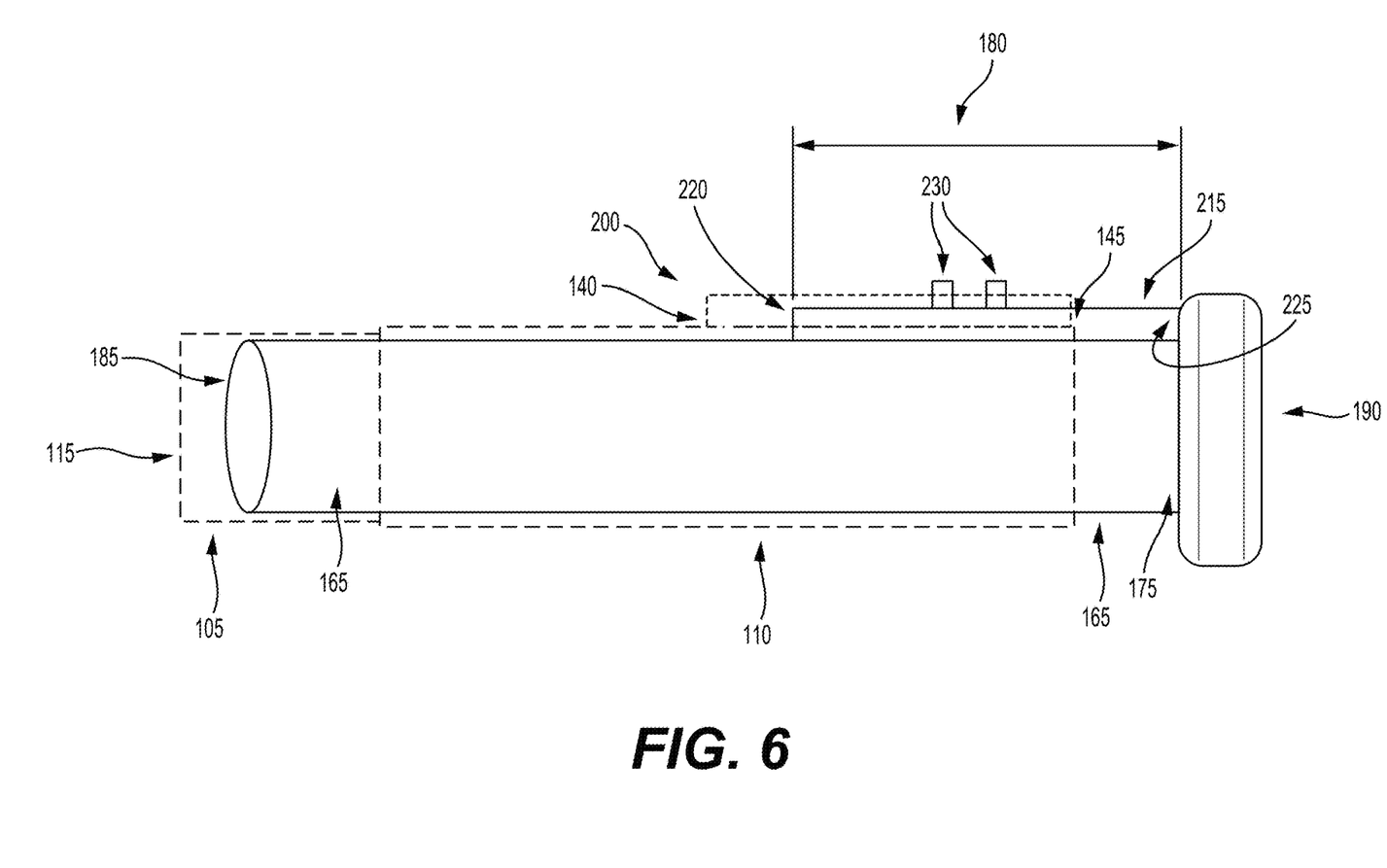
FIG. 6 depicts another side view of the sampling tool with details of the inner body with the first section and the second section.

The sampling tool (100) can also include an inner body (165) as shown in FIGS. 1-2, 4, and 6. The inner body (165) can include a first distal part region (170), a second distal part region (175), and a third part region (180). The third part region (180) can be between the first distal part region (170) and the second distal part region (175) as shown in FIGS. 3 and 6. The first distal part region (170) can include a solid piece (185), as shown in FIG. 3, configured to slidably move out of the first end (115) of the first section (105) and retract into the second section (110) to eject the retrieved and retained at least one sample and to prepare the sampling tool (100) for a subsequent at least one sample to be received therein, respectively.

In FIGS. 1-3, the second distal part region (175) can include a pressable knob (190) configured to slidably move toward and away from, to contact and disengage, respectively, the second end portion (130) of the second section (110). The pressable knob (190) can be further configured to contact a portion of the first elongated slot (150) directly or indirectly.

In an embodiment, the sampling tool (100) can have a first length ($L_1$) of about 6.8 cm and a second length ($L_2$) of about 15 cm as shown in FIG. 4. The first length ($L_1$) is from the second end portion (130) of the second section (110) to an edge of the first end (115) of the first section (105). The second length ($L_2$) is from a top surface of the pressable knob (190) to the edge of the first end (115) of the first section (105) and when the inner body (165) is fully extended away from the second end portion (130) as described herein.

Figure 8:
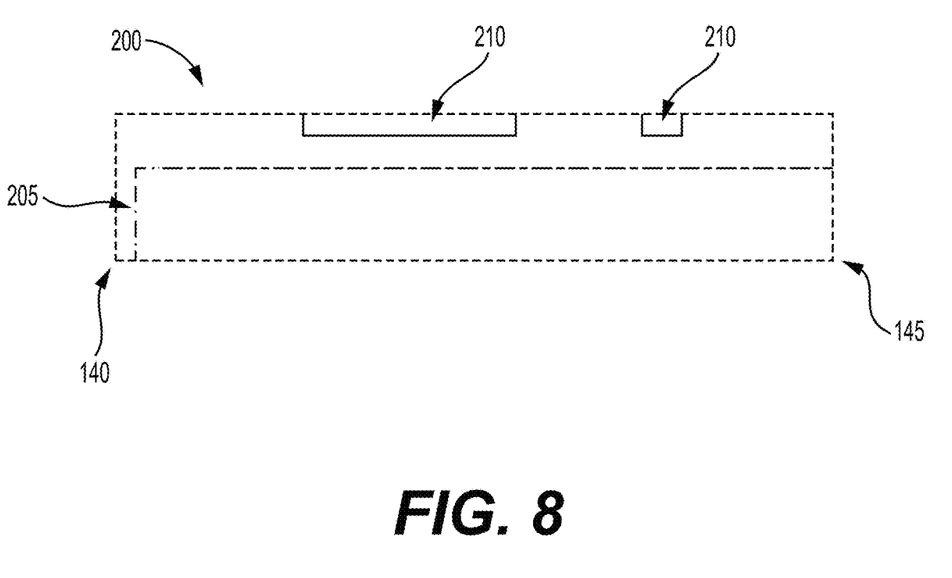
FIG. 8 depicts details of the first elongated raised profile.

In an embodiment, the sampling tool (100) can further include a first elongated raised profile (200) extending from the second periphery region (145) to the first periphery region (140) of the third portion (135) as shown in FIGS. 6-7. A lower region of the first elongated raised profile (200) can include a second elongated slot (205) extending from the second periphery region (145) to about the first periphery region (140) of the third portion (135) as shown in FIG. 8. It is to be understood that the term "about the first periphery region (140)" means "near the first periphery region (140)". In an embodiment, an upper surface of the first elongated raised profile (200) can have at least one recess (210) as shown in FIGS. 1-3 and 8. The at least one recess (210) can include two recesses (210).

In FIGS. 1 and 6-7, the third part region (180) of the inner body (165) can include a second elongated raised profile (215) configured to slidably mate with the first elongated slot (150) of the second section (110) as shown in FIGS. 1 and 6-7. The second elongated raised profile (215) can be further configured to slidably mate with the second elongated slot (205) of the first elongated raised profile (200). As shown in FIG. 6, the second elongated raised profile (215) can include a first end region (220) and a second end region (225). The first end region (220) can be configured to slidably stop at about the first periphery region (140) of the third portion (135). The second end region (225) can be integrally connected to a bottom surface of the pressable knob (190). In an embodiment, the second elongated raised profile (215) can have at least one depressible button (230) configured to engage with the at least one recess (210). The at least one depressible button (230) can include two depressible buttons (230).

In a further embodiment, the present subject matter relates to a method of using the sampling tool (100) above for extracting at least one sample from a medium, the method includes obtaining a medium. Placing the first end (115) of the first section (105) of the sampling tool (100) above an area of interest on the medium. Pressing the first end (115) of the first section (105) into the area of interest on the medium to obtain at least one extracted sample of the medium inside of the first section (105). As a non-limiting example, the sampling tool (100) can be rotated while being lifted vertically to facilitate separation of the at least one extracted sample from a remainder of the medium. Afterward, determining an area to eject the at least one extracted sample of the medium. Placing the first end (115) of the first section (105) above the determined area. Slidably move the solid piece (185) of the first distal part region (170) of the inner body (165) towards and out of the first end (115) of the first section (105) to thereby eject the at least one extracted sample of the medium from the first section (105).

In an embodiment, prior to the pressing step, simultaneously depressing and moving, via a user's finger(s) or thumb, the at least one depressible button (230) away from the at least one recess (210) toward a direction of the second periphery region (145) of the third portion (135) of the second section (110) to retract the solid piece (185) of the first distal part region (170) into the second section (110) as shown in FIGS. 1-2. In this regard, the inner body (165) is fully extended away from the second end portion (130).

In another embodiment, the ejection step can include simultaneously depressing and moving the at least one depressible button (230) away from the at least one recess (210) toward a direction of the first periphery region (140) of the third portion (135) of the second section (110) to slidably move the solid piece (185) of the first distal part region (170) of the inner body (165) towards and out of the first end (115) of the first section (105) to thereby eject the at least one extracted sample of the medium from the first section (105) as shown in FIG. 3.

It is to be understood that the sampling tool and the method of using the sampling tool for extracting at least one sample from a medium are not limited to the specific embodiments described above, but encompass any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A sampling tool comprising:
    an outer body comprising a first section and a second section,
        the first section comprising a first end and a second end, the first end configured to retrieve and retain at least one sample therein,
        the second section comprising a first end portion, a second end portion, and a third portion,
        wherein the third portion is located between the first end portion and the second end portion, and the third portion comprises a first periphery region and a second periphery region,
        wherein a surface of the second periphery region is perpendicular with a surface of the second end portion, the second end of the first section is integrally connected to the first end portion of the second section, and
        wherein the second section comprises a first elongated slot extending from the second end portion to the first periphery region of the third portion; and
    an inner body comprising:
        a first distal part region,
        a second distal part region, and
        a third part region,
        wherein the third part region is between the first distal part region and the second distal part region, the first distal part region comprises a solid piece configured to slidably move out of the first end of the first section and retract into the second section to eject the retrieved and retained at least one sample and to prepare the sampling tool for a subsequent at least one sample to be received therein, respectively,
        wherein the second distal part region comprises a pressable knob configured to slidably move toward and away from, to contact and disengage, respectively, the second end portion of the second section, and wherein the pressable knob is further configured to contact a portion of the first elongated slot.

2. The sampling tool of claim 1, wherein the first elongated slot extends from an outer circumferential surface to an inner circumferential surface of the second section.

3. The sampling tool of claim 1, wherein the pressable knob contacts the portion of the first elongated slot directly.

4. The sampling tool of claim 1, further comprising a first elongated raised profile extending from the second periphery region to the first periphery region of the third portion.

5. The sampling tool of claim 4, wherein a lower region of the first elongated raised profile comprises a second elongated slot extending from the second periphery region to about the first periphery region of the third portion.

6. The sampling tool of claim 4, wherein the third part region of the inner body comprises a second elongated raised profile configured to slidably mate with the first elongated slot of the second section.

7. The sampling tool of claim 6, wherein the second elongated raised profile is further configured to slidably mate with the second elongated slot of the first elongated raised profile.

8. The sampling tool of claim 6, wherein the second elongated raised profile comprises a first end region and a second end region, the first end region is configured to slidably stop at about the first periphery region of the third portion, and the second end region is integrally connected to a bottom surface of the pressable knob.

9. The sampling tool of claim 6, wherein an upper surface of the first elongated raised profile comprises at least one recess; and wherein the second elongated raised profile comprises at least one depressible button configured to engage with the at least one recess.

10. The sampling tool of claim 1, wherein the at least one sample comprises a microorganism sample.

11. The sampling tool of claim 1, wherein the first end and the second end of the first section are made of plastic material.

12. The sampling tool of claim 11, wherein the plastic material is selected from the group consisting of polyethylene, polypropylene, and combinations thereof.

13. A method of using the sampling tool of claim 1 for extracting at least one sample from a medium, the method comprising:
    obtaining a medium;
    placing the first end of the first section of the sampling tool above an area of interest on the medium;
    pressing the first end of the first section into the area of interest on the medium to obtain at least one extracted sample of the medium inside of the first section;
    determining an area to eject the at least one extracted sample of the medium;
    placing the first end of the first section above the determined area; and
    slidably move the solid piece of the first distal part region of the inner body towards and out of the first end of the first section to thereby eject the at least one extracted sample of the medium from the first section.

14. The method of claim 13, further comprising a first elongated raised profile extending from the second periphery region to the first periphery region of the third portion.

15. The method of claim 14, wherein a lower region of the first elongated raised profile comprises a second elongated slot extending from the second periphery region to about the first periphery region of the third portion.

16. The method of claim 14, wherein the third part region of the inner body comprises a second elongated raised profile configured to slidably mate with the first elongated slot of the second section.

17. The method of claim 16, wherein an upper surface of the first elongated raised profile comprises at least one recess; and wherein the second elongated raised profile comprises at least one depressible button configured to engage with the at least one recess.

18. The method of claim 17, wherein prior to the pressing step, simultaneously depressing and moving the at least one depressible button away from the at least one recess toward a direction of the second periphery region of the third portion of the second section to retract the solid piece of the first distal part region into the second section.

19. The method of claim 17, wherein the ejection step comprises simultaneously depressing and moving the at least one depressible button away from the at least one recess toward a direction of the first periphery region of the third portion of the second section to slidably move the solid piece of the first distal part region of the inner body towards and out of the first end of the first section to thereby eject the at least one extracted sample of the medium from the first section.

20. The method of claim 19, wherein the at least one sample comprises a microorganism sample and the medium comprises an agar medium.

* * * * *